(12) United States Patent (10) Patent No.: US 8,480,735 B2
Rigotti et al. (45) Date of Patent: Jul. 9, 2013

(54) INFLATABLE BREAST IMPLANT THAT INDUCES TISSUE GROWTH THROUGH TENSILE STRESS

(75) Inventors: Gino Rigotti, Verona (IT); Guido Baroni, Monza (IT)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/714,293

(22) Filed: Feb. 26, 2010

(65) Prior Publication Data

US 2010/0161052 A1 Jun. 24, 2010

Related U.S. Application Data

(62) Division of application No. 11/957,083, filed on Dec. 14, 2007.

(30) Foreign Application Priority Data

Jun. 1, 2007 (EP) ..................................... 07425339

(51) Int. Cl.
*A61F 2/12* (2006.01)

(52) U.S. Cl.
USPC .................................................. 623/8; 623/7

(58) Field of Classification Search
USPC ......................................................... 623/8, 7
See application file for complete search history.

(56) References Cited

U.S. PATENT DOCUMENTS

| 4,282,954 A | 8/1981 | Hill | |
|---|---|---|---|
| 4,605,691 A | 8/1986 | Balazs | |
| 5,370,691 A * | 12/1994 | Samson | 623/1.22 |
| 5,536,233 A | 7/1996 | Khouri | |
| 5,571,179 A * | 11/1996 | Manders et al. | 623/8 |
| 5,662,583 A | 9/1997 | Khouri | |

(Continued)

FOREIGN PATENT DOCUMENTS

| DE | 4447530 A1 | 3/1996 |
|---|---|---|
| EP | 1997457 A1 | 12/2008 |

(Continued)

OTHER PUBLICATIONS

Shiffman et al. "Fat Transfer Techniques: The Effect of Harvest and Transfer Methods on Adipocyte Viability and Review of the Literature." Dermatologic Surgery. 27: 819-826. 2001.*

(Continued)

*Primary Examiner* — David Isabella
*Assistant Examiner* — Randy Shay
(74) *Attorney, Agent, or Firm* — Linda Fox; Stephen Donovan; Debra Condino

(57) ABSTRACT

A tissue expansion device implanted in a non-activated state over a region of desired tissue growth. Once implanted and positioned the device is activated creating a supporting structure that creates a convex shaped dome over the underlying tissue. The convex shaped dome formed by the tissue expansion device places a tensile stress against the underlying tissue that promotes tissue growth. Alone or with the introduction of tissue enhancing agents and/or adipose tissue, new tissue within the convex shaped void grows until a balance is achieved eliminating the induced stress. Periodically the tissue expansion devices is again activated and enlarged creating an even larger void. Again, the newly enlarged void places additional tensile stress on the underlying tissue thus repeating the cycle of new tissue growth. Once the desired amount of tissue growth has been achieved the device is deactivated and removed.

3 Claims, 7 Drawing Sheets

U.S. PATENT DOCUMENTS

| | | | |
|---|---|---|---|
| 5,669,870 | A | 9/1997 | Elist |
| 5,676,634 | A | 10/1997 | Khouri |
| 5,695,445 | A | 12/1997 | Khouri |
| 5,701,917 | A | 12/1997 | Khouri |
| 5,716,404 | A | 2/1998 | Vacanti |
| 5,972,385 | A | 10/1999 | Liu et al. |
| 6,083,912 | A | 7/2000 | Khouri |
| 6,110,482 | A | 8/2000 | Khouri et al. |
| 6,129,761 | A | 10/2000 | Hubbell |
| 6,146,418 | A * | 11/2000 | Berman ............................ 623/8 |
| 6,206,930 | B1 * | 3/2001 | Burg et al. ................. 623/23.64 |
| 6,478,656 | B1 | 11/2002 | Khouri |
| 6,500,112 | B1 | 12/2002 | Khouri |
| 6,514,200 | B1 | 2/2003 | Khouri |
| 6,641,527 | B2 | 11/2003 | Khouri |
| 6,699,176 | B1 * | 3/2004 | Khouri ............................. 600/38 |
| 6,730,024 | B2 | 5/2004 | Freyre et al. |
| 6,926,667 | B2 | 8/2005 | Khouri |
| 6,991,652 | B2 | 1/2006 | Burg |
| 7,129,209 | B2 | 10/2006 | Rhee |
| 7,316,822 | B2 | 1/2008 | Binette |
| 7,767,452 | B2 | 8/2010 | Kleinsek |
| 7,799,767 | B2 | 9/2010 | Lamberti et al. |
| 7,875,296 | B2 | 1/2011 | Binette |
| 8,053,423 | B2 | 11/2011 | Lamberti et al. |
| 8,137,702 | B2 | 3/2012 | Binette et al. |
| 8,153,591 | B2 | 4/2012 | Masters et al. |
| 2001/0010024 | A1 | 7/2001 | Ledergerber |
| 2002/0198474 | A1 * | 12/2002 | Becker .............................. 601/6 |
| 2003/0152558 | A1 | 8/2003 | Luft et al. |
| 2003/0235603 | A1 * | 12/2003 | Schwarz et al. .............. 424/426 |
| 2003/0236513 | A1 * | 12/2003 | Schwarz et al. ........... 604/890.1 |
| 2003/0236514 | A1 * | 12/2003 | Schwarz .................... 604/890.1 |
| 2005/0025755 | A1 | 2/2005 | Hedrick et al. |
| 2005/0260174 | A1 * | 11/2005 | Fraser et al. ................. 424/93.7 |
| 2005/0267386 | A1 | 12/2005 | Copelan |
| 2006/0161253 | A1 * | 7/2006 | Lesh ................................ 623/8 |
| 2007/0104695 | A1 | 5/2007 | Quijano et al. |
| 2007/0148766 | A1 | 6/2007 | Yoshimura et al. |
| 2007/0251531 | A1 | 11/2007 | Khouri |
| 2008/0103518 | A1 * | 5/2008 | Karmon ......................... 606/192 |
| 2008/0167613 | A1 | 7/2008 | Khouri et al. |
| 2008/0300681 | A1 * | 12/2008 | Rigotti et al. ..................... 623/8 |
| 2009/0093878 | A1 * | 4/2009 | Glicksman ........................ 623/8 |
| 2009/0098177 | A1 | 4/2009 | Werkmeister et al. |
| 2009/0123547 | A1 | 5/2009 | Hill et al. |
| 2009/0124552 | A1 | 5/2009 | Hill et al. |
| 2009/0162415 | A1 | 6/2009 | Huang et al. |
| 2009/0175516 | A1 | 7/2009 | Moraunt et al. |
| 2009/0181104 | A1 | 7/2009 | Rigotti et al. |
| 2010/0160948 | A1 | 6/2010 | Rigotti et al. |
| 2010/0168780 | A1 | 7/2010 | Rigotti et al. |
| 2010/0249924 | A1 | 9/2010 | Powell et al. |
| 2011/0008406 | A1 | 1/2011 | Altman et al. |
| 2011/0008436 | A1 | 1/2011 | Altman et al. |
| 2011/0008437 | A1 | 1/2011 | Altman et al. |
| 2011/0014263 | A1 | 1/2011 | Altman et al. |
| 2011/0014287 | A1 | 1/2011 | Altman et al. |
| 2011/0020409 | A1 | 1/2011 | Altman et al. |
| 2011/0052695 | A1 | 3/2011 | Jiang et al. |
| 2011/0070281 | A1 | 3/2011 | Altman |
| 2011/0097381 | A1 | 4/2011 | Binette |
| 2011/0111031 | A1 | 5/2011 | Jiang et al. |
| 2011/0150823 | A1 | 6/2011 | Huang |
| 2011/0150846 | A1 | 6/2011 | Van Epps |
| 2011/0189292 | A1 | 8/2011 | Lebreton et al. |
| 2012/0010146 | A1 | 1/2012 | Han et al. |
| 2012/0045420 | A1 | 2/2012 | Van Epps et al. |
| 2012/0076868 | A1 | 3/2012 | Lamberti et al. |
| 2012/0156265 | A1 | 6/2012 | Binette et al. |
| 2012/0164116 | A1 | 6/2012 | Van Epps |
| 2012/0165935 | A1 | 6/2012 | Van Epps |
| 2012/0171265 | A1 | 7/2012 | Altman et al. |
| 2012/0172317 | A1 | 7/2012 | Altman et al. |
| 2012/0172985 | A1 | 7/2012 | Altman et al. |
| 2012/0207837 | A1 | 8/2012 | Powell et al. |
| 2012/0209381 | A1 | 8/2012 | Powell et al. |
| 2012/0213852 | A1 | 8/2012 | Van Epps et al. |
| 2012/0213853 | A1 | 8/2012 | Van Epps et al. |
| 2012/0219627 | A1 | 8/2012 | Van Epps et al. |
| 2012/0263686 | A1 | 10/2012 | Van Epps et al. |
| 2012/0265297 | A1 | 10/2012 | Altman et al. |
| 2012/0269777 | A1 | 10/2012 | Van Epps et al. |

FOREIGN PATENT DOCUMENTS

| | | |
|---|---|---|
| WO | WO 94/25056 A2 | 11/1994 |
| WO | WO 95/33502 A1 | 12/1995 |
| WO | WO 96/34615 A1 | 11/1996 |
| WO | WO 96/40172 A1 | 12/1996 |
| WO | WO 98/55047 A1 | 12/1998 |
| WO | WO 00/32084 A2 | 6/2000 |
| WO | WO 2004/067065 A1 | 8/2004 |
| WO | WO 2006/006169 A2 | 1/2006 |
| WO | WO 2006006169 A2 * | 1/2006 |
| WO | WO 2007/102635 A1 | 9/2007 |
| WO | WO 2007/124478 A2 | 11/2007 |
| WO | WO 2009/003135 A1 | 12/2008 |
| WO | 2011072399 | 6/2011 |

OTHER PUBLICATIONS

Roger Khouri, et al., "Breast Reconstruction and Augmentation Using Pre-Expansion and Autologous Fat Transplantation," Clin Plas Surg 36 (2009) 269-280.

Roger Khouri, et al., "Nonsurgical Breast Enlargement Using an External Soft-Tissue Expansion System," Plastic and Reconstructive Surgery, Jun. 2000, vol. 105 No. 7, pp. 2500-2512.

Sumner Slavin, Discussion, "Nonsurgical Breast Enlargement Using an External Soft-Tissue Expansion System," Plastic and Reconstructive Surgery, Jun. 2000, pp. 2513-2514.

David M. Brown, et al., "Osteochondral Allografts With an Intramedullary Muscle Flap in Rabbits," Clinical Orthopaedics and Related Research, Jan 1997, No. 334, pp. 282-290.

Steven E. Chavoustie, et al., "Breast Augmentation With Grafting of Liposuctioned Fat—A Safe and Effective Procedure," Obstetrics and Gyneclogy, Apr. 2007, vol. 109, No. 4.

Shiffman "Fat Transfer Techniques:The Effect of Harvest and Transfer Methods on Adipocyte Viability and Review of the Literature." Dermatologic Surgery. 27:819-826 2001.

Ramon "Enhancing the Take of Injected Adipose Tissue by a Simple Method for Concentrating Fat Cells" In: Plast Reconst Surg. Jan. 2005 vol. 115, No. 1, pp. 197-201.

Gomillion "Stem Cells and Adipose Tissue Engineering," In: Biomaterials Dec. 2006, vol. 27, pp. 6052-6063. especially p. 6054 table 3, p. 6057.

* cited by examiner

US 8,480,735 B2

INFLATABLE BREAST IMPLANT THAT INDUCES TISSUE GROWTH THROUGH TENSILE STRESS

CROSS REFERENCE TO RELATED APPLICATIONS

This is a divisional of U.S. patent application Ser. No. 11/957,083, filed on Dec. 14, 2007, which application is based on and claims priority under 35 U.S.C. §119 to European patent application number 07425339.4, filed Jun. 1, 2007, the entire disclosures of which are incorporated herein by this specific reference.

BACKGROUND OF THE INVENTION

1. Field of the Invention

Embodiments of the present invention relate, in general, to expansion of tissue and particularly to biological tissue growth through tensile stress induced by unidirectional radial expansion of an implantable/removable device.

2. Relevant Background

It is well known that tissue growth can be initiated and sustained in response to a sustained tensile stress. Stress is defined as a force distributed over a finite area. The imposition of such a tensile force (stress) has taken many forms and has resulted in human tissue growth in many kinds of living tissue including skin, bone, muscle, nerves, blood vessels, lungs, and the like. The devices that create such a tensile force to promote tissue growth include hooks, springs, and other mechanical devices that attach to the various portions of the tissue so as to apply a sustained tension. These techniques are typically associated with reconstructive surgery, in which a portion of the human anatomy has been damaged and often require sustained non-ambulatory care. For this reason, procedures of this type for cosmetic surgery have not gained much acceptance and thus surgical implants are typically used. The use of implants does not create an environment supportive of tissue growth. As is described below, an implant is placed in a dissected region to fill an artificially created void. The implant thus becomes pseudo new tissue, eliminating the natural impetuous for tissue growth.

Non-invasive versions of devices offering ambulatory care to promote tissue growth are known in the art but have yielded inconsistent and minimal results. The non-invasive devices known in the art provide an irregular and inconsistent application of a slight suction to the skin in an attempt to produce a tensile force on the applicable tissue. In doing so the non-invasive procedure seeks uncontrolled and undirected tissue growth in the general region subjected to the suction.

While successful in promoting some tissue growth, non-invasive techniques share the common barrier of requiring daily user interaction resulting in inconsistent and often asymmetrical results. Additionally, it is well known that for tissue growth to occur, a tensile force should be applied on a consistent basis for extended periods of time. Misapplication of the device or inconsistent use, especially in the early stages of treatment, deters tissue generation. Devices of this type are typically cumbersome and awkward and restrict the user's day-to-day activity.

With respect to invasive techniques, the challenge has been to create a targeted environment for tissue growth that is both effective and yet allows the patient to continue with their day-to-day activities. In the past, inflatable devices have been utilized to dissect tissue layers to create an anatomic working space to facilitate the performance of laparoscopic or other minimally invasive surgical procedures including implantation. A surgical balloon dissector is inserted in a region and inflated to create a void in which an implant is placed. In contrast to traditional blunt dissection techniques, the dissection balloon creates the tissue pocket while respecting natural tissue planes or boundaries in the anatomy.

A second type of inflatable device or balloon, known as a tissue expander, has been utilized as a temporary implant to gradually expand a previously dissected pocket over time as the overlying skin and tissue gradually alters and expands in response to the fluid filled tissue expander. Such tissue expanders are typically left in place over a prolonged period of time to allow the cutaneous tissues to gradually alter and expand. Accordingly, periodic adjustment of the expander to add additional fluid is required as the tissue gradually expands over time. While growth in the skin and surrounding tissue is promoted, tissue growth in the void rarely occurs because the pocket or void is filled with the relatively solid tissue expander.

Breast augmentation has traditionally occurred using the aforementioned techniques followed by inserting one of two types of implants—silicone or saline. Saline implants are filled at the time of surgery with saline solution. Implants of this type can be inserted through very small incisions in a deflated form and after they are in place in the body, can be inflated to their final size. Silicone implants, which are implanted in their inflated state, are firmer and more noticeable beneath thin soft tissue and therefore, in most instances require placement underneath the pectoralis major muscle (sub pectoral placement). This adds to the length and complexity of the surgical procedure and time for surgical recovery. Both procedures require a foreign object, the implant, to remain within the body as no actual breast tissue is grown.

SUMMARY OF THE INVENTION

Briefly stated, embodiments of the present invention involve implanting a removable device into the human body that promotes new tissue growth. A tissue expansion device is implanted over a region of desired tissue growth. The device during implantation is in a non-activated, deflated state. Once implanted and positioned over the region of desired tissue growth the device is activated. In one embodiment of the present invention fluid is injected into one or more toroidal, spiral, or other shaped vessels of the tissue expansion device. The vessels are encased within an outer and inner membrane. These membranes, along with the structural construction of the vessels, create a supporting structure that, in one embodiment, creates a convex shaped dome or a void space under the inner membrane of the tissue expansion device.

The dome or void formed by the tissue expansion device places a tensile force against the overlying tissue. To accommodate this tensile force the overlying tissue, in most cases the dermis, stretches or lengthens by forming new tissue. In a similar manner the convex shaped tissue expansion device creates a void beneath the device which in turn places a tensile stress on the tissue underlying the tissue expansion device such as by creating a vacuum or suction pressure or force that pulls up on the underlying tissue (e.g., due to differential pressures between the void or pocket and the environment exterior to the progressively or stepwise inflated or expanded device). This induced tensile stress promotes tissue growth. Alone or with the introduction of tissue enhancing agents, new tissue within the convex shape grows until a stress balance is achieved. Once the tensile stress has been removed due to new tissue growth, future growth is constrained. Accordingly, the tissue expansion device is once again activated and enlarged creating an even larger void (or new void space as old or original void space is filled with growth of underlying tissue). The newly enlarged void places a renewed tensile stress on the underlying and overlying tissue thus repeating the cycle of new tissue growth.

Upon the desired volume of new tissue growth being achieved, the tissue expansion device is deactivated. In one embodiment of the present invention, deactivation occurs by extracting fluid from within the toroidal vessels that comprise the tissue expansion device. Subsequent to deactivation, the tissue expansion device is extracted from the region via a minimally invasive surgical procedure.

Another aspect of the present invention is the external application of the tissue expansion device to a particular region of the body. In this embodiment of the present invention, the tissue expansion device is affixed to the outer surface of the skin in its deflated state using a medical adhesive or similar product. The bond between the skin and the device formed by the adhesive creates an air tight seal. As fluid is injected into the device, chambers within the device expand to create a dome-like or convex shape. As the underlying surface of the device is drawn up into the convex shape, the affixed skin is also carried into the created void. The resulting gentle suction or tensile force on the skin creates a pocket of reduced pressure and suction between the inner and outer layer of cutaneous tissue. This continuous tensile force promotes tissue growth within the region to fill the void and remove the area of reduced pressure and tension from the body. As the region reaches equilibrium through expanded tissue growth, additional fluid is injected into the device further expanding the convex shape and reestablishing the area of tension. As in the embodiment in which the tissue expansion device was implanted into the body, the expansion of the device continues until the desired amount of new tissue growth has been achieved. Once the desired volume of tissue growth has been achieved, the device is deflated via the removal of fluid and is detached from the surface of the skin.

In another embodiment of the present invention the application of the tissue expansion device, either in its implanted application or as externally affixed to the surface of the skin, is combined with agents promoting tissue growth. As used herein and with respect to various embodiments of the present invention the term "agents" is to be broadly construed and includes, but is not limited to, adipose tissue (autologous and non-autologous) in its non-purified and purified form and/or adipose tissue enhanced with cells or other pharmaceuticals promoting tissue growth. These agents are injected into the void created by the tissue expansion device. In another embodiment these agents include stem cells, progenitor cells, adipose-derived cells including endothelial cell precursors (not stem cells), and other proliferating cells (including differentiation-committed cells and other regenerative cells). These agents are injected into the void to promote tissue growth. Each of these agents, alone or in combination, can be injected into the void created by the tissue expansion device to promote tissue growth.

In one embodiment of the present invention, adipose tissue, preferably but not necessarily harvested from the patient, is injected into the void created by the tissue expansion device of the present invention. Typically, adipose tissue is harvested from a patient's buttocks, abdomen or thighs. According to one embodiment of the present invention, non-purified adipose tissue, harvested from the patient, is injected into the void while in another embodiment of the present invention the adipose tissue is purified and/or divided into portions. According to this embodiment of the present invention, a first portion of the tissue is reserved while the second is processed to isolate and extract stem cells. The extracted stem cells are then combined with the first, reserved portion of the purified adipose tissue creating a purified adipose tissue specimen that is enhanced with extracted stem cells. In another embodiment of the present invention non-purified adipose is harvested and combined with isolated and extracted stem cells as described above. In another embodiment of the present invention adipose derived cells including committed endothelia cell precursors and other proliferating cell types known to one skilled in the art can be either combined with adipose tissue or injected into the void created by the tissue expansion device separately to promote new tissue growth. Various growth factors can also be injected. Indeed any combination of these and other agents, tissues, and/or cells used in combination with the tissue expansion device is contemplated by the present invention.

Adipose tissue and/or other agents, as previously defined, are introduced into the void created by the tissue expansion device via one or more injections. As new tissue is formed and the stress within the void is reduced or eliminated, the tissue expansion device is expanded through the introduction of additional fluid into the structural members of the tissue expansion device. The newly expanded tissue expansion device recreates a region of tensile stress on the area of desired tissue growth. At substantially the same time, one or more additional injections of adipose tissue and/or other agents for promoting tissue growth are introduced into the recreated or expanded void to once again promote tissue growth. This process repeats until the desired volume of new tissue is achieved.

The features and advantages described in this disclosure and in the following detailed description are not all-inclusive, and particularly, many additional features and advantages will be apparent to one of ordinary skill in the relevant art in view of the drawings, specification, and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

BRIEF DESCRIPTION OF THE DRAWINGS

The aforementioned and other features and objects of the present invention and the manner of attaining them will become more apparent and the invention itself will be best understood by reference to the following description of a preferred embodiment taken in conjunction with the accompanying drawings, wherein.

Figure 1:
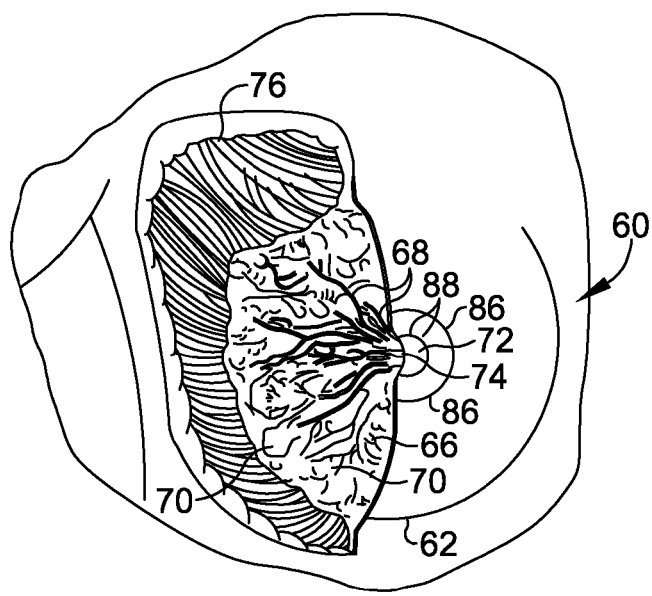
FIG. 1 is a front view of the anatomy of the human breast with a portion showing subcutaneous detail.

The Figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

Specific embodiments of the present invention are hereafter described in detail with reference to the accompanying figures. Like elements in the various figures are identified by like reference numerals for consistency. Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention.

As previously described, all types of human tissue will grow and generate new, normal tissue when subjected to gentle, sustained, uniform tension. Tension, or stretching, is the mechanism involved in normal growth, regeneration, and normal balance of human tissue. This process is the body's own natural mechanism for growth and healing. For instance, a cut in one's hand results in the area around the cut becomes tight. To heal the wound, the body places tension on the area, making it tight and thereby activating cell replication until the area is healed.

According to one embodiment of the present invention, and as demonstrated in laboratory testing, a minimally invasive tissue expansion device generates within a specific region of the body a sustained state of tensile stress, which causes underlying tissue to grow. The device gently and gradually draws the tissue forward causing it to grow in response to the sustained tension. This "drawing" may be based on suction or vacuum forces developed in the void defined by the inner membrane of the expansion device such as by creating a desired differential between pressure interior to the device and exterior to the device. The sustained mechanical tension (stress) is translated to the cell via biochemical signals causing cellular growth which develops new generated tissue. Normal balance (i.e., no stress) is then restored after the new tissue is grown.

Ligaments, such as the inframammary ligament in the breast, join fascia and skin. The human fascia is simply a band or sheath of connective tissue investing, supporting, or binding together internal organs or parts of the body. In certain areas of the body such as the breast, points of fusion between layers of fascia create well-defined boundaries which may be used to advantage by the surgeon during dissection, particularly balloon dissection, to create an anatomically well-defined space between layers joined by such ligaments. Ligaments have been identified which create such useful boundaries in, for example, the breast, forearm, leg, and brow. Surgeons, particularly plastic surgeons and others skilled in the art, will understand that the principles described herein have application to any body region where such fascial boundaries exist. While many of the embodiments disclosed are discussed with particular reference to generation of breast tissue, one skilled in the art will note that these embodiments are exemplary in nature and that the techniques and concepts presented herein can be used to promote any soft tissue growth throughout the body. Moreover, one skilled in the art will understand that the principles described herein have application to various other surgical procedures (e.g., treatment of carpal tunnel syndrome) in which the promotion of tissue growth would be beneficial.

As is known, the mammary ligaments form a circumferential ligament about the breast to form a circumferential fusion between the superficial fascia and the deep fascia. This connective ligament which completely surrounds the breast to form a circular boundary to the cleft between the superficial fascia and deep fascia is referred to herein as the circumferential mammary ligament. The circumferential mammary ligament forms a natural boundary connecting two tissue layers that a surgeon dissecting between the layers may use to define and limit the extent of the dissection. It has been found that these defined layers also offer a region for tissue growth as disclosed herein.

Figure 2:
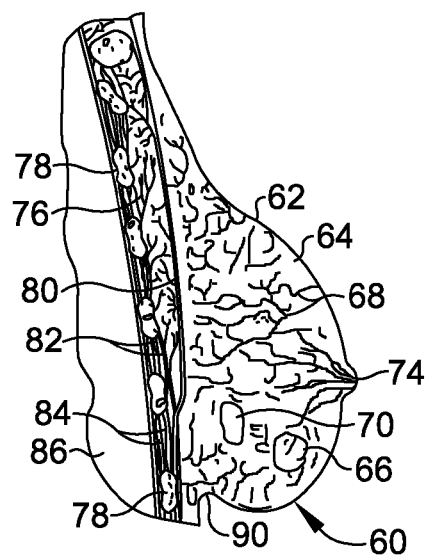
FIG. 2 is a cross-sectional view of the anatomy of the human breast showing subcutaneous layers down to the rib cage.

Referring initially to FIGS. 1 and 2, front and side views of the anatomy of the human breast 60 are illustrated. An epidermis layer 62 overlies the dermis layer 64. Underneath the dermis layer 64 is a layer of subcutaneous fat 66. Suspensory ligaments 68 are positioned within the layer of subcutaneous fat 66 to hold breast 60 in an upright position. Gland lobules 70 are arranged radially about the nipple 72. Each gland lobe 70 has its own lactiferous duct 74 opening on the nipple 72. Nipple 72 is surrounded by areola 88. The pectoralis major muscle 76 covers the chest wall and ribs 78, and is covered by a layer of superficial fascia 80. Intercostal muscles 82 are shown situated between ribs 78 and surrounding intercostal vessels and nerve 84. The lung 86 is positioned behind ribs 78.

Figure 3:
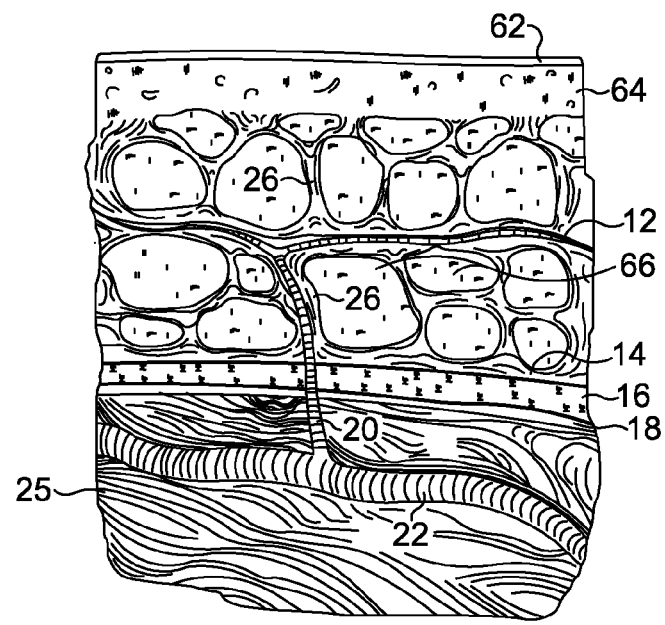
FIG. 3 is a cross-sectional view of an exemplary portion of human anatomy showing the fascial cleft between the superficial fascia and deep fascia.

Turning to FIG. 3, a cross-sectional view of the anatomy of the human cutaneous tissue particularly illustrating a fascial cleft between the superficial fascia and the deep fascia is shown. Superficial vessels 12 within the fat layer 66 are connected to perforating vessels 20 which in turn are connected to deep vessels 22. Vertical cutaneous ligaments 26, joining tissue layers, are also shown within the fat layer 66. Muscle 25 is covered by a thin layer of deep fascia 18. The fat layer 66 is sheathed by a thin layer of superficial fascia 14. A naturally occurring tissue plane or fascial cleft 16 (shown as a gap in FIG. 3; however, prior to dissection no gap exists) occurs between the superficial fascia 14 and deep fascia 18. This fascial cleft 16 may be viewed as potential space within the human body which may be fluently dissected by dissecting balloons to create an anatomic cavity. It has been found that the ligaments joining these tissue layers define the boundaries of the potential space and limit the potential space created during balloon dissection.

Figure 4:
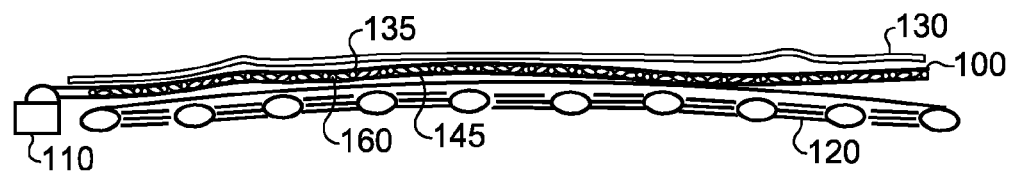
FIG. 4 is a simplified cross-sectional view of human cutaneous tissue illustrating the implantation and orientation of a tissue expansion device for the creation of a tissue pocket according to one embodiment of the present invention.

Accordingly, to one embodiment of the present invention, and with additional reference to FIG. 4, a tissue expansion device 100 is implanted between an outer layer 130, such as glandular breast tissue, and an inner layer 120, such as underlying fascia, so as to create an environment supportive of tissue growth. According to one embodiment of the present invention an axillary incision is made with tunneling medially and interiorly performed from the axillary incision to a desired location underlying the glandular breast tissue. The tissue expansion device 100 is advanced and then positioned into the naturally occurring potential space between the inner layer fascia 120 and the outer layer glandular breast tissue 130. Alternatively, the tissue expansion device can be positioned between the superficial fascia and the deep fascia defining a naturally occurring tissue plane. Dissection along such naturally occurring tissue planes is desirable in that a virtually bloodless space may be created. While many of the examples and Figures in the present invention describe the application of the present invention to create an environment for tissue growth in connection with breast augmentation or the growth of breast tissue, one skilled in the relevant art will understand that the tissue expansion device and techniques presented herein can be utilized in numerous other applications and locations throughout the body to promote the growth of tissue.

The tissue expansion device 100 also comprises an access site 110 to allow fluid to be inserted into the device 100. The access site can be a fixture that extends from the device 100 above the epidermis or it can be sub dermis and accessible via per-cutaneous injections. The injected fluid inflates structures within the tissue expansion device 110 to create a convex form similar to that of a dome under the resistance of the overlying tissue. According to one embodiment of the present invention the tissue expansion device 100 comprises an inflatable/expandable region 160 or vessel encased by an outer layer or membrane 135 and an inner layer or membrane 145. The use of the term "dome" is intended to be construed relatively broadly to cover nearly any void formed by the expansion device 110. It is foreseen for example that the void shape may be a disk or plate with a particular thickness defined by the depth or height of the inflated wall of the device 110 with a circular, oval, elliptical, or other shaped periphery. In other words, the dome may be thought of as a relatively thin plate or void that is incrementally or progressively stepped farther away from the original tissue or tissue surface underlying the device 110 gradually increasing in volume as the tissue grows toward the inner membrane 145 of the device 110 (and, then, it is again inflated to pull the tissue out to cause additional growth until a desired regrowth volume is achieved).

According to one embodiment of the present invention, the tissue expansion device 100 in its activated, inflated or "on" state resembles that of a convex dome. The size of the dome (the tissue expansion device) is controlled by the amount of fluid injected into the device. A dome is a common structural element that resembles the hollow upper half of a sphere and typically possesses a circular plane. And while domes can be constructed or configured so as to exert equal forces in all directions, they do not have to be perfectly spherical in cross-section. For example, a dome may also be a section through an ellipse. If the baseline is taken parallel to the shorter of an ellipse's two diameters, a tall dome results, giving a sense of upward reach. A section across the longer axis results in a low dome, capping the volume instead. A dome can also be considered as an arch which has been rotated around its vertical axis.

A dome is convex in shape with a hollow concave interior. Unlike conventional balloon dissection or implants, the concave space underneath the tissue expansion device (dome) of the present invention remains open and void. The distribution of force by the tissue surrounding the void produces the tensile stress within the void responsible for new tissue growth. The tensile stress found within the interior region of the void is a product of differential pressures distributed by the tissue expansion device. As the tissue expansion device increases in size, the skin or tissue overlaying the device becomes taught and exerts an equal and opposite resistance to the expansion. These forces are translated to the tissue supporting the base of the tissue expansion device. The region beneath the void experiences a reduced internal pressure as compared to the pressure exerted against the tissue expansion device and normal undisturbed tissue. The reduced internal pressure within the void translates to the underlying tissue as a subtle pulling or tensile force distributed throughout the voided region. This tensile stress promotes tissue growth. Again, one skilled in the art will recognize that the shape of the tissue expansion device may vary while remaining equally effective at producing new tissue growth. Accordingly, the size and shape of the device can be configured to address other anatomical areas of the human body. In each of these designs the resulting structure provides a hollow convex shaped object or void that promotes tissue growth beneath.

Figure 5A:
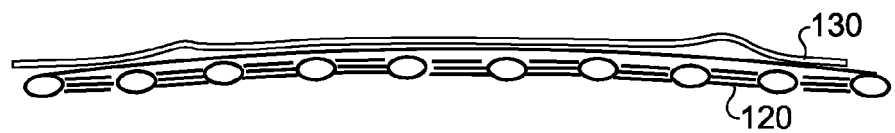
FIGS. 5A through 5D are simplified cross-sectional views of the same human cutaneous tissue illustrating the progressive creation of a concave tissue pocket according to one embodiment of the present invention through the use of a tissue expansion device.
Figure 5B:
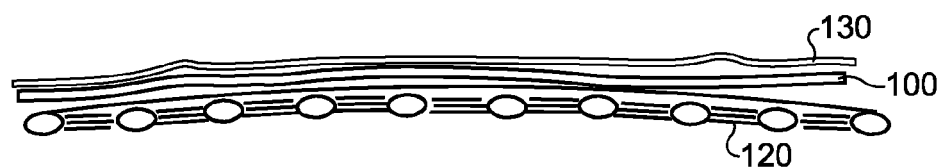
Figure 5C:
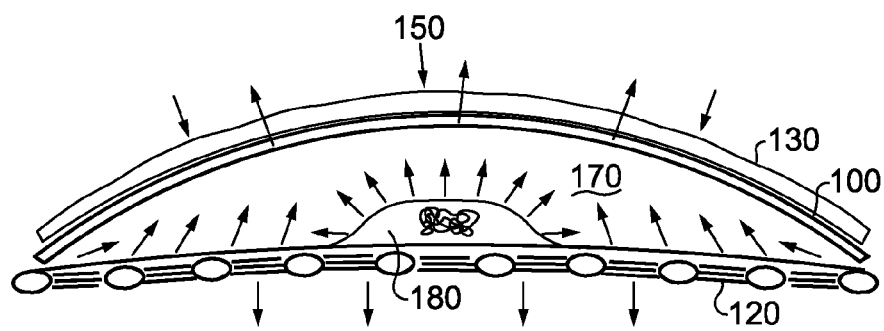

With reference to FIGS. 5A through 5D, progressive steps of application of the present invention for a tissue expansion device 100 can be observed. FIG. 5A represents a simplified cross-sectional view of the anatomy of the human cutaneous tissue comprising an outer layer 130 and an inner layer 120 as it would exist in its pre-implantation state. FIG. 5B shows the same cutaneous tissue subsequent to a minimally invasive surgical procedure in which a tissue expansion device 100 has been inserted between the inner layer 120 and the outer layer 130 of tissue. In its deflated or "off" state the tissue expansion device minimally displaces the surrounding tissue. FIG. 5C shows the same section of cutaneous tissue with the tissue expansion device 100 in an expanded mode. Through an access site (not shown), fluid is injected into the tissue expansion device 100 causing it to create a convex or dome-like shape. The inflated shape of the tissue expansion device 100 can vary according to its particular application. FIGS. 5A through 5D represent a progressive general cross-sectional demonstration of the present invention.

The convex shape of the inflated tissue expansion device 100 is formed by a balancing of forces represented by the various force arrows 150. The outer layer of tissue 130 resists the expansion of the device 100. Similarly, the lower layer of the tissue 120 resists being displaced into the concave void 170 formed by the convex shape of the tissue expansion device 100 placing it in a certain degree of tensile stress. The degree upon which the tissue expansion device is expanded is controlled by an attending physician but in general is gradual in nature so as to prevent or minimize any trauma from occurring at the site. The resulting opposing forces 150 and the void 170 encased by the tissue expansion device 100 on one side and the lower tissue layer 120 on the other forms an environment for new tissue growth 180.

As new tissue grows 180 within the void 170 created by the tissue expansion device 100, the tensile stress on the inner layer 120 is reduced and ultimately eliminated. Once the tensile stress is eliminated the impetus for new tissue growth fades and the region is once again in balance. Similarly the outer layer 130 also experiences some degree of new tissue growth as the skin or dermis layer is stretched to accommodate the increased volume created by the tissue expansion device 100. While the region is under tension the void 170 is filled by a biological serum as the body attempts to alleviate the stress induced by the tissue expansion device. In such an instance, and according to one embodiment of the present invention, tissue regeneration may be provoked or enhanced within the void 170 by the introduction of agents allowing cellular cultures and/or tissue to be grown within the biological serum. As previously described, the application of the tissue expansion device 100, either in its implanted application or as externally affixed to the surface of the skin, is combined with agents promoting tissue growth. These and other techniques to assist and encourage the growth of new tissue within the generated void 170 are contemplated to be utilized in conjunction with the use of the tissue expansion device 100 described herein.

In one embodiment of the present invention new tissue growth 180 is promoted by the gradual introduction of adipose tissue into the void 170 produced by the tissue expansion device 100. Adipose tissue, or fat, is typically loose connective tissue composed of adipocytes. In one exemplary embodiment of the present invention adipose tissue is injected into the void 170. The adipose tissue can be either autologous or non-autologous and can be injected into the void 170 in either purified or non-purified form. One or more agent injections, such as adipose tissue, can be done over an extended period of time with varied volumes so as to both promote tissue growth and reduce complications such as capsular contracture.

According to yet another embodiment of the present invention Adipose tissue, preferably harvested from the patient, is divided into one portion that is reserved for later use and a second portion which is purified to extract stem cells. The purification process generally involves centrifugation at a spin speed and spin time selected to not only separate water and triglycerides from the harvested adipose tissue but to also damage or cause lesions in a portion of the mature adipocytes in the adipose tissue. Interestingly, the purification process does not attempt to maintain mature adipocytes in a relatively undamaged condition, but it instead is designed to further damage a portion of these mature adipocytes in the adipose tissue to hasten their clearance by the patient's body after implantation. The water, triglycerides, and oil from the damaged, mature adipocytes (as well as other byproducts or tissue components) are separated from the now purified adipose tissue and discarded leaving behind extracted stem cells. The extracted stem cells from the second portion are then combined with the first reserved portion to produce a non-purified adipose tissue specimen that is enhanced with an increased concentration of stem cells. This process aids in replacing adipocytes that may have been damaged during the harvesting of the adipose tissue thus promoting tissue growth. This accentuated mixture of adipose tissue and stem cells is then injected into the void 170.

In addition to harvesting the patient's (or other donor) adipose tissue, the procedure for procurement and treatment of adipose tissue or lipoaspirate according to one embodiment of the present invention includes purifying the tissue without the need to externally isolate and culture stem cells. As previously described, the lipoaspirate purification procedure is designed to remove a large part of the triglycerides stored in the harvested adipose tissue and to separate adipose tissue (i.e., the purified adipose tissue) from its water content and from the oil produced by the destruction of the damaged adipocytes. An advantage of use of the inventive purification technique is that there is no need for any kind of cell culture to grow additional tissue outside the patient's body. Avoiding such external culturing better controls risks of micro-organism contamination, reduces the complexity of the tissue preparation process, and controls or limits associated costs. A further advantage of the purification or tissue preparation process is that the process does not require the technically challenging step of isolating or extracting adipose-derived stem cells (ADAS) but instead allows the ADAS to remain in their natural support structure or 3D scaffold which facilitates vascularization and other benefits.

In clinical trials, the introduction of purified adipose tissue has produced promising results. The tissue transfer process included selecting an area as the donor site (e.g., the medial area of the knee, the abdominal area, buttocks, or the trochanteric area) and then infiltrating the area with a cold saline solution with the addition of 15 cc of adrenalin and 20 to 30 cc of lidocaine 0.5% per 500 cc. Adipose tissue was removed using a cannula with a 2 mm diameter and a 3 cc syringe. According to one embodiment, the syringes were placed directly in a centrifuge that was then set at 2700 rpm and run for 15 minutes, which resulted in separation of purified adipose tissue for injection from its water content and from oil resulting from the destruction of damaged adipocytes. As previously described, the layer of oil and residual liquid (including triglycerides) were discarded. The adipose tissue was implanted in the same patient using an injection cannula with a 1 mm diameter in single tunnels or pathways made by following a pre-surgical plan or model of the injection points and pathways to ensure substantially uniform distribution of the ADAS or purified adipose tissue.

Large amounts of triglycerides present in the transferred tissue generates unwanted granulomas. Hence, the tissue transfer method of the present invention includes, according to one embodiment, a purification procedure that is aimed at removing a large part of the triglycerides stored in the harvested tissue. The purification process disclosed herein reduces the risk of contaminations with micro-organisms associated with cell culturing. In addition, the stem cells or ADAS are maintained in a natural or existing 3D scaffold or support structure that favors reconstruction of a microvascular bed. Ultrastructural examination of the adipose tissue performed after the purification procedure confirms the presence of well-preserved elements in the vasculo-stromal component, which was composed of endothelial cells and mesenchymal stem cells in perivascular sites. Residual mature adipocytes remaining in the purified adipose tissue showed interruptions of the cytoplasmic membrane and presented various degrees of degeneration ranging up to cellular necrosis.

According to one embodiment of the present invention, the stem cells of the purified adipose tissue target the damaged areas or area subjected to the increased tensile forces. In a second or later stage, the stem cells excrete angiogenic factors that lead to the production of new microvessels that, in turn, hydrate the tissue as newly formed vessels tend to be hyperpermeable. The chain of events leading to: "mesemchymalization" of the tissue, hence, targeting of damaged or stressed areas by stem cells (which is favored by direct and uniform injection into the affected areas as compared with clump or less uniform distribution techniques) are; release of angiogenic factors; formation of new vessels; and hydration. This process favors the development of ADAS in mature adipocytes. After injection of the adipose tissue, a newly formed microcirculation replaces the existing microcirculation.

The injection of the enhanced adipose tissue is generally performed with a syringe or similar device. A pre-surgical plan including the injection points and pathways provides the surgeon with the map for intra-operative guidance or aiming to achieve a high level of uniformity of adipose tissue deposition, which is typically purified adipose tissue. The pre-surgical plan would benefit nearly any tissue transfer or implant such as non-purified adipose tissue, adipose tissue with additional stem cells, or other tissues/cells (e.g., mesenchymal cells, especially smooth or skeletal muscle cells, myocytes (muscle stem cells), chondrocytes, adipocytes, fibromyoblasts, ectodermal cells, or nerve cells which may or may not be dissociated). Further, growth factors, angiofactors, anti-inflammatories, selective growth inhibitors, and the like may also be provided with or after implantation of the tissue. Tissue and cells are preferably autologous cells, obtained by biopsy and expanded in culture, although cells from close relatives or other donors may be used such as with appropriate immunosuppression. Immunologically inert cells, such as embryonic cells, stem cells, and cells genetically engineered to avoid the need for immunosuppression may also be used.

In other embodiments of the present invention, agents introduced into the void 170 include pharmaceutical stimuli, specimens of non-differentiated stem cells, differentiated stem cells, endothelial cell precursors, and/or other proliferating cells (including differentiation-committed cells).

The overall volume of agents injected into the void may vary widely to practice the invention according to embodiment presented herein and with each patient. As an example, the average size of a breast implant is in the range of 325 to 400 cc, and it may be desirable to prepare up to 400 cc or more of an agent such as purified adipose tissue to perform a breast reconstruction or augmentation. Indeed several injections of differing volumes of agents described herein may be utilized in combination with increased tension from the tissue expansion device 100 until the desired volume of tissue growth or tissue expansion has occurred.

Figure 5D:
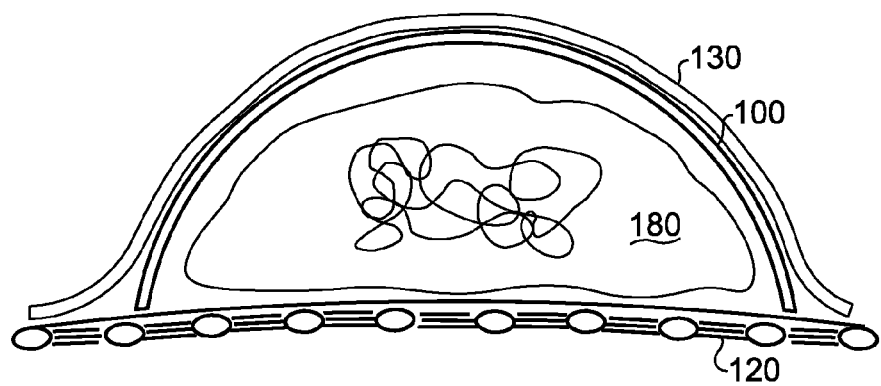

Prior to a complete balance of forces 150 (e.g., pressures) occurring due to the growth of new tissue 180 and/or the injection of tissue promoting agents, the tissue expansion device 100 is once again expanded (as shown in FIG. 5D) thus expanding the void 170 and recreating the tensile stress imposed on the outer tissue layer 130 and the inner tissue layer 120. This process replicates until the desired amount of expansion and corresponding new tissue growth within the void 170 has occurred. Clinical trials have shown that for permanent tissue growth to occur, the induced stress and expansion process should occur consistently over several weeks or months. With respect to promoting breast tissue, the void 170 may need to be expanded to a volume of 325 to 400 cubic centimeters or greater to replicate an average breast implant. As previously discussed the volume of the void is increased gradually over time to promote continual tissue growth until the desired result is achieved.

Once the desired amount of growth has occurred and the forces 150 induced by the tissue expansion device 100 have been eliminated due to new tissue growth 180, the tissue expansion device 100 can be removed, leaving behind the newly grown natural tissue. The present invention enables tissue growth to occur at specific targeted areas at an increased rate with minimal patient involvement. Additionally, while the exemplary figures and corresponding discussion present a symmetrical domelike or conical shaped device, the present invention is equally applicable to other geometric shapes so long as a convex region or a void can be created beneath the device.

Figure 6A:
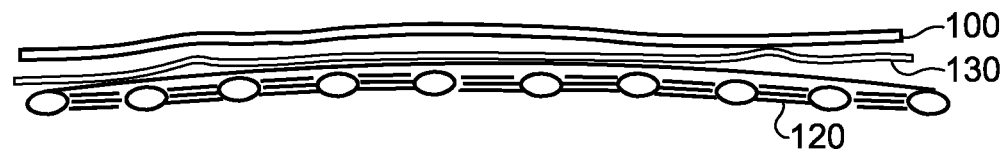
FIGS. 6A through 6C are simplified cross-sectional views of the same human cutaneous tissue illustrating the progressive creation of a concave tissue pocket according to one embodiment of the present invention through the use of an external overlay tissue expansion device.
Figure 6B:
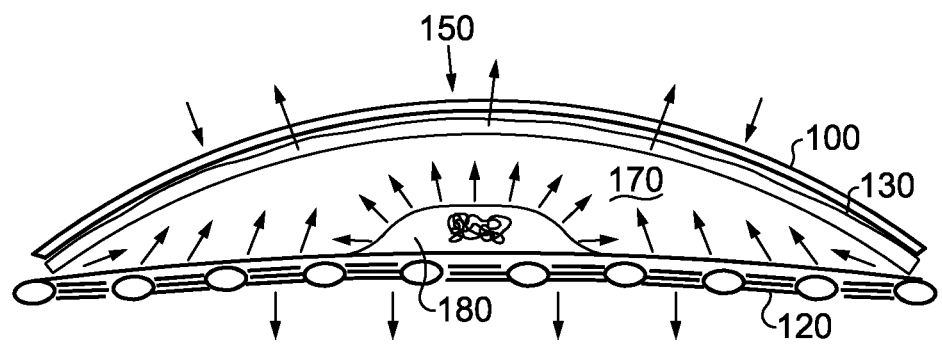
Figure 6C:
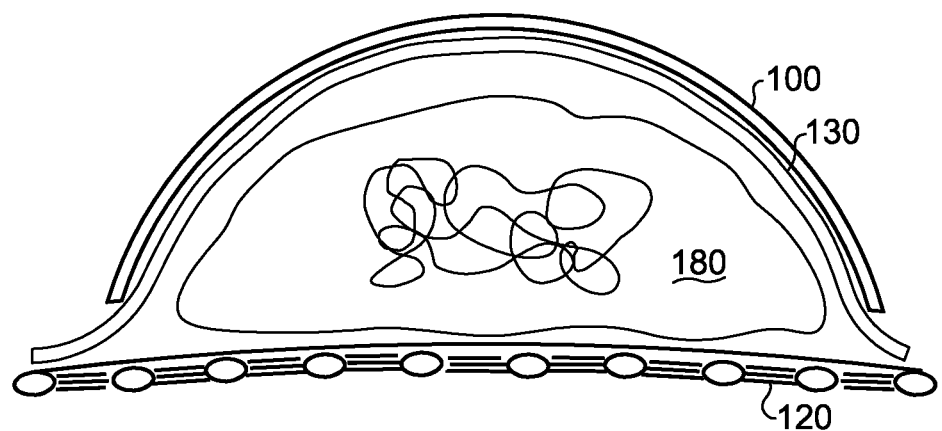

According to another embodiment of the present invention, as shown in FIGS. 6A through 6C, a tissue expansion device 100 can be overlaid upon the region of desired tissue growth. As in FIGS. 5A through 5D, FIGS. 6A through 6C represent a simplified cross-sectional view of human cutaneous tissue. In this embodiment of the present invention, the tissue expansion device is affixed to the outer surface of the outer layer of the cutaneous tissue (skin). The device 100 can be affixed to the outer layer of the skin by a variety of adhesives as would be known to one skilled in the medical art. The affixation of the device 100 to the skin is both durable and flexible so as to enable the skin to expand with the growth of the underlying tissue 180 and the void formed by expansion of the tissue expansion device 100. The bond created between the skin and the device 100 creates a seal so as to create a region of negative pressure upon the activation and expansion of the tissue expansion device as is described in the following paragraphs.

In its deflated condition the tissue expansion device 100 simply conforms to the natural shape of the underlying tissue 130. As fluid is injected in the device 100, the expandable sections of the device fill to create a convex or dome-like shape. The gradual expansion of the device 100, as shown in FIG. 5B, produces a region of diminished pressure or a gentle suction effect upon the region that promotes tissue growth 180 beneath. Again, the tissue growth 180 is experienced in the void region created between the outer layer 130 and the inner layer 120 of cutaneous tissue. The device 100 is affixed to the skin such that it remains firmly attached even as the skin stretches and grows to accommodate the newly formed tissue 180 beneath. Depending on the desired volume of tissue growth and the number of injections of fluid into the device, the tissue expansion device 100 can be deflated, removed and then reaffixed in a new application to the underlying skin. In such a manner, the underlying skin is able to stretch/grow and accommodate the tissue growth 180 without being impeded by the adhesive or other material that is used to affix the device 100 to the skin.

As the desired volume of tissue growth 180 is achieved, the device 100 can be permanently removed without any risk of an invasive procedure. This external application embodiment can be easily applied to any region of the body and be designed to provide a preferential direction of expansion. While much of the discussion of the present invention focuses on the implanted embodiment, one skilled in the art will recognize that the concepts disclosed herein are equally applicable to those embodiments of the invention that utilize an external application of the tissue expansion device 100.

Furthermore, the injection of agents such as pharmaceutical stimuli, stem cell in-situ cultures and/or adipose tissue can be also be introduced into the void produced by the external tissue expansion device to promote new tissue growth. The consistent and continual presence of a tensile stress (suction) on the skin surface combined with periodic and gradual injections of agents disclosed herein can promote rapid and permanent tissue growth.

Another aspect of the present invention is the prevention or treatment of capsular contracture. After an implant is placed into the body, especially in the breast region, tissue surrounding the implant can harden and squeeze the implant. The hardening that can occur is due to excess scar tissue formation and contraction of that tissue around the implant. The viscosity of the fluid within the implant itself remains unchanged. Scar tissue that forms around the implant causes the breasts or other tissue to harden (similar to what a contracted muscle feels like) as the naturally forming scar tissue around the implant tightens and squeezes it. While capsular contracture is an unpredictable complication, it is also the most common complication of breast augmentation.

The introduction of the disclosed agents including adipose tissue in conjunction with the use of the tissue expansion device can prevent and/or minimize the instance of capsular contracture. With respect to embodiments of the present invention involving the implantation of the tissue expansion device, the addition of the adipose tissue, according to one embodiment of the present invention, not only promotes tissue growth within the void but minimizes or prevents the encapsulation of the expansion device. Furthermore, at the termination of the procedure, with the desired tissue growth achieved, the tissue expansion device is removed preventing any future risk of capsular contracture. This advantage is even more prominent with respect to the exterior application of the tissue expansion device. With no foreign body being introduced into the body, the risk of capsular contracture is entirely eliminated.

According to another embodiment of the present invention, capsular contracture can be effectively treated using the tissue expansion device. As previously discussed, capsular contracture is a condition associated with a physiological reaction to the introduction of an implanted foreign body. According to one method embodiment of the present invention, capsular contracture can be treated by creating a voided region in the tissue surrounding a previously placed implant, (the area experiencing capsular contracture) and introducing into that region an agent such as an adipose tissue specimen. In such an exemplary embodiment of the present invention, the tissue expansion device is positioned either external to the dermis or implanted between layers of subcutaneous tissue over a region experiencing capsular contracture.

Once the tissue expansion device is positioned over the area of interest, it is expanded to create a tensile force on the tissue resulting in a voided area near or immediately adjacent to the capsular contracture tissue. An adipose tissue specimen or other agent or combination thereof can then be injected into the void to promote new tissue growth. In another embodiment of the present invention, the inflation of the tissue expansion device occurs in conjunction with a deflation of the existing implant to expand the voided region bilaterally.

Recall that capsular contracture describes hardened tissue surrounding an implant. By relieving the pressure of the implant caused by the constricting tissue through extraction of the implant's contents and the use of the tissue expansion device creating a tensile or pulling stress on the tissue away from the implant, a void can be created in the region of capsular contracture.

Agents, including adipose tissue, injected into this void can reduce and/or eliminate the capsular contracture by promoting new, normal tissue growth. The continued tensile stress maintained by the tissue expansion device aids in the adipose tissue's ability to treat the condition. As with the previously described applications of the tissue expansion device, the adipose tissue specimen introduced to treat capsular contracture can be purified or non-purified and is ideally harvested from the patient. The adipose tissue can also be enhanced by adding stem cells gained through a separate purification process or grown via culture. Ideally, a portion of a harvested specimen of adipose tissue is purified via centrifugation to remove a large part of the triglyceride stored in the tissue and to cause lesion in the thin cytoplasmic sheets of the mature adiposities. The combination of the tensile stress and the adipose tissue specimen works together to promote new tissue growth and relieve capsular contracture. In one embodiment, stem cells are maintained in their natural three-dimensional scaffold that favors the reconstruction of a microvascular bed.

The result of such a combined treatment is growth of structural normal adipose tissue (i.e. normal fat tissue). As tissue grows, additional enlargement of the tissue expansion device to reestablish the void combined with supplemental injections of adipose tissue specimens act to reduce or eliminate capsular contracture as well as continued deflating of the previous device. As the capsular contracture is treated, the previous (causing) implant can be completely deflated and/or extracted leaving natural normal adipose tissue.

Figure 7:
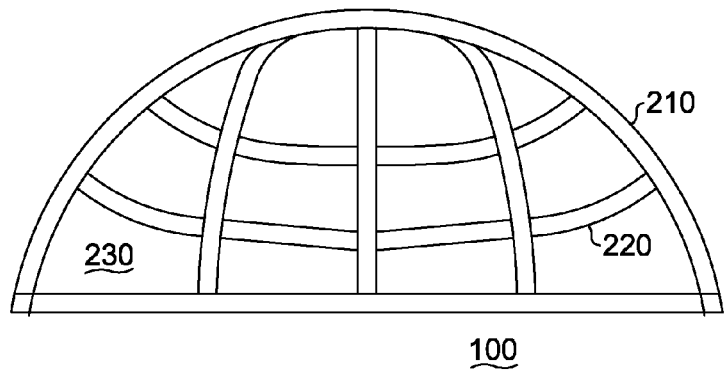
FIG. 7 is a cross-sectional view of one embodiment of the present invention of a tissue expansion device possessing load bearing structures.

FIG. 7 is a cross-sectional view of one embodiment of the present invention of a tissue expansion device 100 possessing load bearing structures. With a post implantation of the tissue expansion device 100, it is important that the shape of the inflated device be consistent and controllable. While in one embodiment of the present invention the shape of the device is controlled by injection of fluids in a confined space within two membranes, other embodiments of the present invention may use memory shape materials such as Nitinol or polymers that can be activated, or any other material or structure that can create a progressively larger inner cavity.

As shown in FIG. 7, one embodiment of the present invention possesses both lateral 220 and vertical 210 support members. These support members are joined by a connective fabric 230 or membrane capable of transferring the forces induced by the resistance of the outer tissue layer 130 on the tissue expansion device 100 to the support members 210, 220 and ultimately to the base of the tissue expansion device and the surrounding tissue. The support structures 210, 220 and the connective fabric 230 are, in one embodiment of the present invention, encased by inner 145 and outer 135 membranes. Assuming that the outer layer 130 of cutaneous tissue imposes on the tissue expansion device 100 a uniform and distributed force 150, and knowing the desired shape of the tissue expansion device 100 at its various stages of expansion, the configuration of support members 210, 220 can be determined using conventional engineering techniques that are well known in the art. Furthermore, by varying the size (volume) of the supporting members, and pressure barriers between subsequent sections of the supporting structure, the incremental infusion of fluid into the supporting members can create a progressively increasing void 170 or dome centered around, in this example, the vertex of the device 100. Other designs and configurations can be constructed to accommodate tissue growth in a non-symmetric fashion.

Figure 8A:
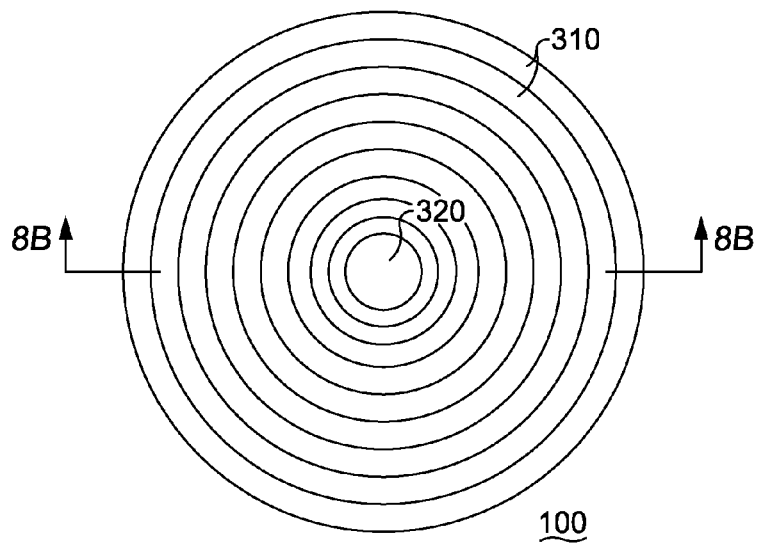
FIGS. 8A and 8B illustrate, respectively, a top, or planar view and cross-sectional view of a tissue expansion device employing overlying toroidal members encased in a thin-walled pressure vessel for the creation of a convex tissue pocket according to one embodiment of the present invention.
Figure 8B:
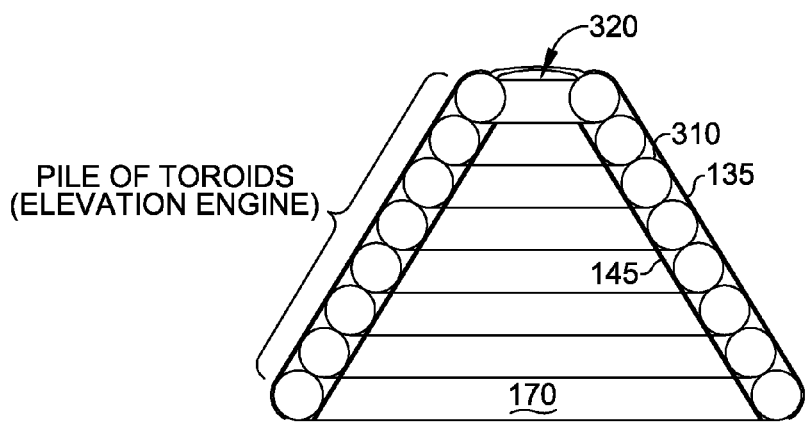

FIGS. 8A and 8B are, respectively, a top or planar view and cross-sectional view of a radial expansion device for the creation of a convex tissue pocket according to one embodiment of the present invention. A series of concentric toroids 310, or revolutions of a closed circle (in this embodiment) about an axis, describes one embodiment of a tissue expansion device 100. The toroids 310, each with a slightly larger overall diameter, are encased within an inner 145 membrane and an outer 135 membrane. Access to each toroid allows the shape of the void 170 created by the inflation of the toroids 310 to be controlled creating an elevation engine. Access 320 to the concave region beneath the device, the void 170, can be achieved through the center of the uppermost toroidal ring.

Figure 9A:
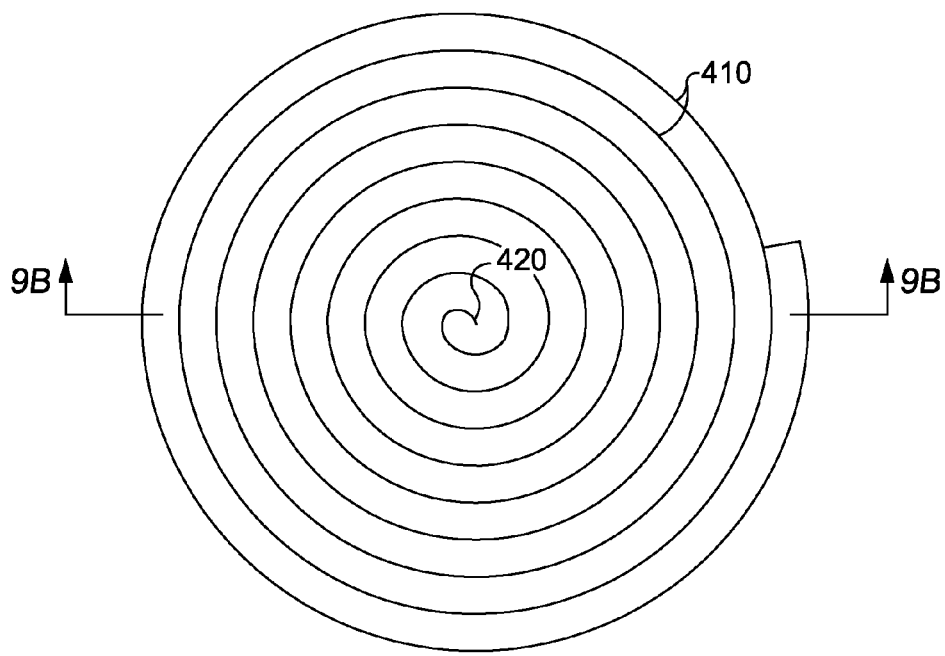
FIG. 9A is a cross-sectional view of one embodiment of the present invention of a tissue expansion device employing a single spiral vessel encased in a thin walled pressure vessel for the creation of a convex tissue pocket.

FIG. 9A is a cross-sectional view of one embodiment of the present invention of a tissue expansion device employing a single spiral vessel encased in a thin-walled pressure vessel (membranes) for the creation of a convex tissue pocket 170. As opposed to the previous embodiment that comprised a plurality of toroidal members 310, this embodiment of present invention is comprised of a single toroidal member 410 constructed in a spiral configuration. The single toroidal member 410 concentrically spirals from a central access point 420 to a diameter sufficient to cover the targeted tissue growth area. The toroidal member 410 is further encased between an outer membrane 135 and an inner 145 membrane. The membranes 135, 145 and indeed the toroidal member itself 410 are designed to be of sufficient strength to withstand the internal and external pressures exerted on the tissue expansion device 100 in any orientation.

Figure 9B:
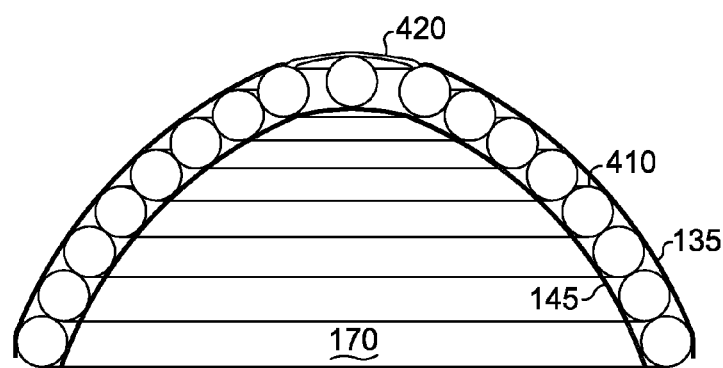
FIG. 9B is a planer, or top view of the embodiment of the present invention shown in FIG. 9A for a tissue expansion device employing a single spiral vessel encased in a thin walled pressure vessel.

FIG. 9B is a planer view of the embodiment shown in FIG. 8 for a tissue expansion device employing a single spiral vessel encased in a thin-walled pressure vessel. Again, a single toroidal vessel 410 is configured to achieve a concentric spiral shape encased within a pair of membranes 135, 145. Calculation of such stress and strain in thin-walled cylindrical vessels closed at both ends is well known as is that of an ellipsoid under a uniform internal or external pressure. The calculations should be completed for any possible orientation that the user may experience to take into account the effects of gravity and the effects of dynamic loads. For example, pressures within a single toroidal vessel 410 implanted to promote the growth of breast tissue would be uniformly increased due to gravity when the patient in which the device was implanted was in the prone (lying on their back) position. A vector representing the force of gravity would act substantially and uniformly perpendicular to the base of the tissue expansion device while forces exerted by the outlying tissue and those of the interior void act orthogonal to the surface of the device. Accordingly, and as will be appreciated by one skilled in the art, the spirals or members of the toroidal vessel 410 near the top of the device share forces driving the design of the device.

Similarly, as the origination of the patient changes, the pressure within the toroidal vessel 410 changes due to the reorientation of the vector representing gravity. With the patient in the standing position, gravity forces are distributed to the lower or first spirals of the toroidal vessel 410. Furthermore, dynamic loads should be considered to ensure that the tissue expansion device remains both safe and functional.

As mentioned, access to the tissue expansion device is in one embodiment of the present invention through a central access point. In the embodiment shown in FIGS. 8A and 8B, this access point is near the center or vertex of the resulting dome. Additional fluid can be inserted into the toroidal vessel via per-cutaneous injections to provide a slow and consistent sustained tensile stress to the lower cutaneous layer. Once the desired volume of new tissue has been grown within the resulting void 170 the fluid within the single toroidal tissue expansion device can be withdrawn. Thereafter the tissue expansion device 100 can be removed leaving behind the newly grown permanent tissue and no foreign body.

Figure 10:
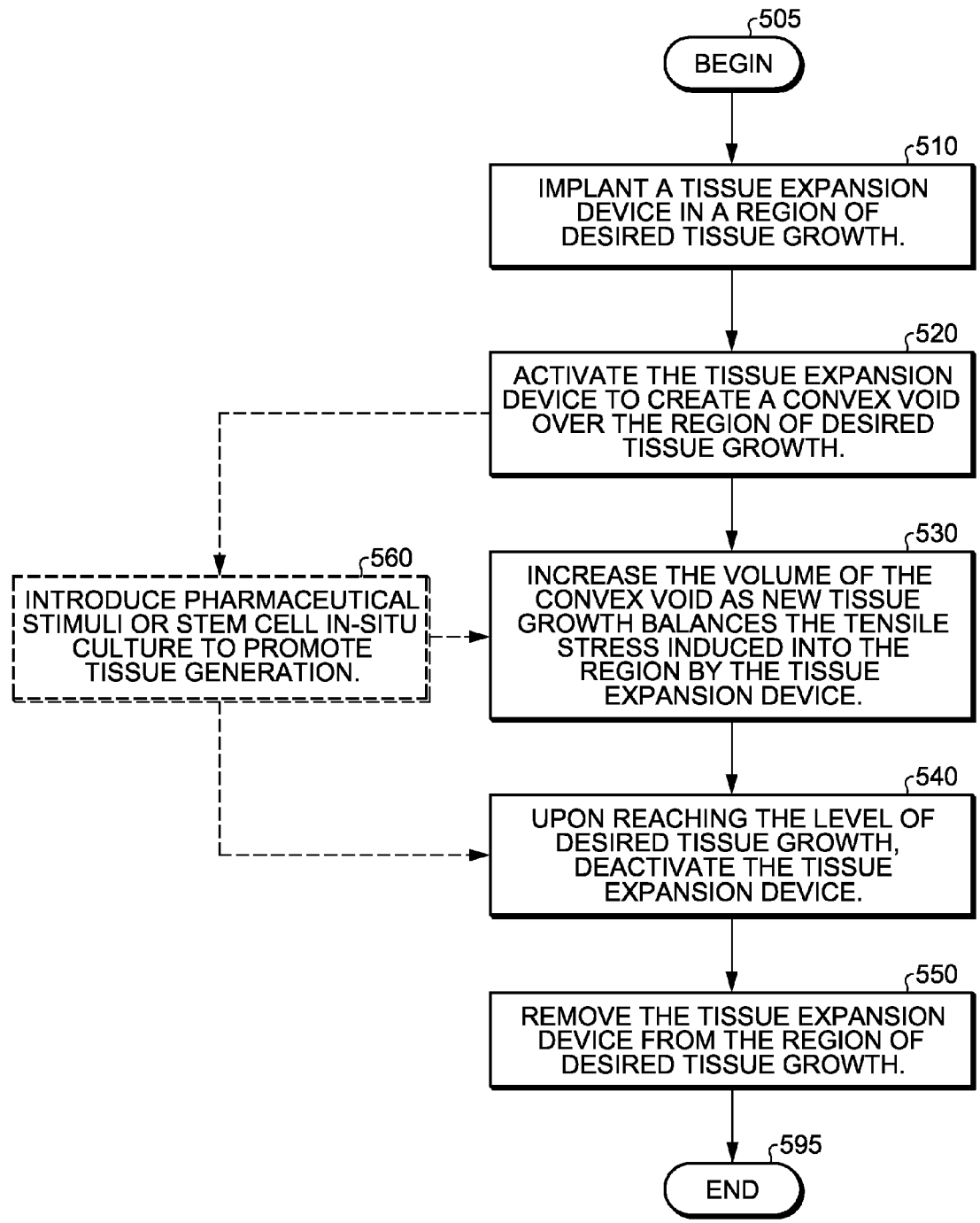
FIG. 10 is one method embodiment for promoting tissue growth using a tissue expansion device according to the present invention.

FIG. 10 is a flowchart illustrating one method embodiment of an exemplary process for biologically expanding tissue using a tissue expansion device 100 according to the present invention. It will be understood that each block of the flowchart, and combinations of blocks in the flowchart, represent a specific function or functionality or specific process objective. Accordingly, blocks of the flowchart support combinations of means for performing the specified functions and combinations of steps for performing the specified functions. It will also be understood that each block of the flowchart, and combinations of blocks in the flowchart, can be implemented differently without detracting from the intent and novel features of the present invention.

FIG. 10 begins 505 with either the external positioning or the internal placement 510 of a tissue expansion device 100 over a region of desired new tissue growth. Once positioned the tissue expansion device is activated 520. As previously discussed, activation may include the injection of a fluid into one or more toroidal members encased within two membranes such as polymers or may involve shape memory material such as, but not limited to, Nitinol. The activation of the tissue expansion device causes the device to form a convex or dome shape above the region of desired tissue growth drawing the tissue into the device thus creating beneath a void or region under stress. The void thus induces a tensile stress on the underlying tissue promoting new tissue growth. The activation of the device, according to one embodiment of the present invention, may be through repetitious injections of fluid into a single toroidal vessel through a common access point or, according to another embodiment of the present invention, through multiple injections of multiple toroidal vessels via a plurality of access points. Indeed any combination of these options may be employed to activate the tissue expansion device in an incremental manner so as provide the necessary shape and underlying tensile stresses to promote tissue growth.

As new tissue grows to occupy the void created by the tissue expansion device, the forces, and thus the tensile stress, exerted on the underlying tissue diminishes. The diminished stress reduces the impetuous to grow new tissue. To maintain new tissue growth in the desired region, volume of the convex shape of the tissue expansion device is increased 530. In one embodiment of the invention predefined volumes of fluid are added to the device according to a defined schedule. Initially a larger volume of injection may be necessary to create the necessary tensile stress to promote tissue growth. Later increments may require substantially less of an injection to provide a similar environment conducive to tissue growth. In other embodiments, the amount of expansion and the time of expansion are based on the rate of tissue growth. The added volume within the void caused by the increased size of the tissue expansion device restores the tensile stress on the underlying tissue. Typically the added volume to the tissue expansion device is accomplished via percutaneous injections of fluid into the tissue expansion device's supporting structure by a physician.

Again tissue growth is promoted until a balance, or elimination, of forces is achieved. This process of balanced forces due to new tissue growth followed by an increase in the size of the tissue expansion device revitalizing the tensile stress and promoting more tissue growth continues until a desired amount, volume, of new tissue growth has occurred. In other embodiments of the present invention, agents, such as pharmaceutical stimuli, adipose tissue, and/or stem cell in-situ cultures and the like, can be introduced 560 into the void below the tissue expansion device and in contact with the underlying tissue to promote tissue growth.

Once the new tissue growth has stabilized the tissue expansion device is deactivated 540 by, in one embodiment of the present invention, the removal of the fluid contained with the toroidal member(s). Again the removal of the fluid can be accomplished by a percutaneous injection (withdrawal) at a physician's office or similar medical facility. Once deactivated the tissue expansion device is removed 550 from the region of new tissue growth terminating 595 the procedure and leaving behind newly grown tissue without the presence of any foreign objects. Again the removal of the tissue expansion device from the region of tissue growth (fascial cleft) is a minimally invasive procedure conducted at a medical facility with respect to the internal implementation while removal of the external tissue expansion device can likely be accomplished in a suitable outpatient facility or physician's office. In yet another embodiment of the present invention, the tissue expansion device may remain within the body but in its deflated state. As the tissue expansion device is deflated it fails to provide an impetus for tissue growth and the risks of leaving the implant within the body should be weighted against the risks and cost of the procedure for its removal.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

We claim:

1. An implantable tissue expander device for promoting tissue growth in a breast of a human being, the device comprising:

an inner membrane;

an outer membrane;

wherein the inner membrane and the outer membrane define a thin-walled pressure vessel which forms an inner surface and an outer exterior surface of the device respectively; and an inflatable hollow cylindrical vessel in the form of a spiral, encased within the outer membrane and the inner membrane and the vessel being expandable upon inflation thereof between a substantially planar deflated state and an inflated state in the form of a dome having a vertex with the outer membrane positioned external to the dome and the inner membrane positioned internal to the dome, with a concave region being formed below the vertex and external to the inner membrane, said tissue expander being structured to form a void within breast tissue and external to the device when the device is implanted in a breast and inflated.

2. The device of claim 1, further comprising an access site to allow fluid to be inserted into the vessel.

3. The device of claim 2 wherein the access site is located in a center of the spiral and near the vertex of said dome when the vessel is in the inflated state.

* * * * *